US00PP32484P2

(12) United States Plant Patent
Avent

(10) Patent No.: US PP32,484 P2
(45) Date of Patent: Nov. 17, 2020

(54) ***AGAVE* PLANT NAMED 'GREAT WHITE SHARK'**

(50) Latin Name: ***Agave* x *nikelima***
Varietal Denomination: Great White Shark

(71) Applicant: Tony Avent, Raleigh, NC (US)

(72) Inventor: Tony Avent, Raleigh, NC (US)

( * ) Notice: Subject to any disclaimer, the term of this patent is extended or adjusted under 35 U.S.C. 154(b) by 0 days.

(21) Appl. No.: 16/602,888

(22) Filed: Dec. 18, 2019

(51) Int. Cl.
*A01H 5/12* (2018.01)
*A01H 6/12* (2018.01)

(52) U.S. Cl.
USPC ..... Plt./373

(58) Field of Classification Search
USPC ..... Plt./373
See application file for complete search history.

*Primary Examiner* — Susan McCormick Ewoldt

(57) ABSTRACT

A new and unique *Agave* plant named 'Great White Shark' characterized by upright, curving, linear to obovate foliage that is pinched to folded in the apical portion. The leaves are variegated with a wide creamy-yellow margin and dark gray-green center and have small, firm, darkly-colored teeth only in the basal portion and a dark apical spine.

3 Drawing Sheets

Botanical classification: *Agave* x *nickelima.*
Variety denomination: 'Great White Shark'.

BACKGROUND OF THE INVENTION

The present invention relates to the new and distinct *Agave* plant, *Agave* x *nickelima* 'Great White Shark' discovered by the inventor at a specialty nursery in Raleigh, N.C., USA as an uninduced whole-plant mutation from a tissue cultured crop of *Agave* 'Sharkskin Shoes' (not patented) in the summer of 2009. *Agave* x *nickelima* is an interspecific hybrid between *A. nickelsiae* and *A. asperrima*. The new plant has been successfully asexually propagated by division of basal offshoots at the same nursery in Raleigh, N.C. Division of basal offshoot asexual propagation has been found to produce stable and identical plants that maintain the unique characteristics of the original plant.

A non-enabling photograph of the new plant was first shared in early 2019 on a website maintained by Plant Delights Nursery, Inc. Plant Delights Nursery, Inc. obtained the photograph and all information about the new plant from the inventor. No plants of *Agave* 'Great White Shark' have been sold, in this country or anywhere in the world, prior to the filing of this application, nor has any disclosure of the new plant been made prior to the filing of this application with the except that which was disclosed within one year of the filing of this application and was either derived directly or indirectly from the inventor.

BRIEF SUMMARY OF THE INVENTION

*Agave* 'Great White Shark' differs from its parent, 'Sharkskin Shoes', as well as all other *Agaves* known to the applicant. 'Sharkskin Shoes' has foliage with a dark gray-green color. The most similar *Agave* cultivars known to the inventor are: 'Ripple Effect' U.S. Plant Pat. No. 30,281, 'Royal Flush' U.S. Plant Pat. No. 31,138 and 'Desert Diamond' U.S. Plant Pat. No. 26,384. 'Ripple Effect' has a flatter habit, broader leaves, larger teeth and the marginal variegation has more greenish white mixed with the creamy-yellow. 'Royal Flush' has flatter leaves with more outright habit and the leaf margins have filifers. 'Desert Diamond' has shorter, obovate and broader foliage with a smaller habit. 'Great White Shark' also has leaves that are pinched to folded at the terminal ends and curve upwards in the distal half.

*Agave* 'Great White Shark' differs from all other *Agaves* known to the applicant, by the combination of the following traits:

1. Upright curving foliage, pinched to folded near apical portion;
2. Leaves have wide creamy-yellow margins and contrasting dark gray-green leaf centers;
3. Leaf margins have small, firm, darkly-colored teeth in the basal portion only and a dark apical spine.

BRIEF DESCRIPTION OF THE DRAWINGS

The drawings of the new plant demonstrates the overall appearance of the new plant including the unique traits as a ten-year-old plant grown in a container in a winter greenhouse and outdoor garden in the summer, with supplemental water and fertilizer as needed. The colors are as accurate as reasonably possible with color reproductions. Ambient light spectrum, temperature, source and direction may cause the appearance of minor variation in color.

DETAILED BOTANICAL DESCRIPTION

Figure 1:
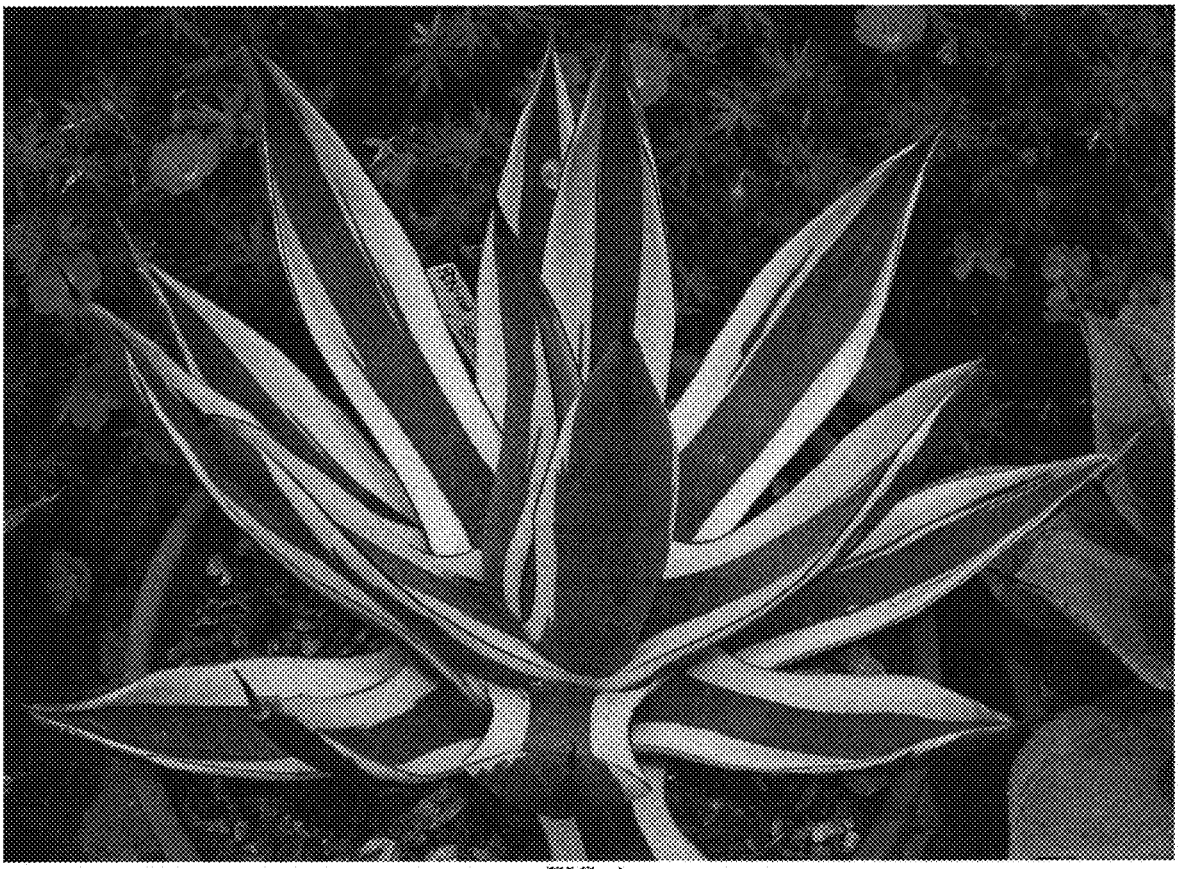
FIG. 1 shows the habit of the new plant.
Figure 2:
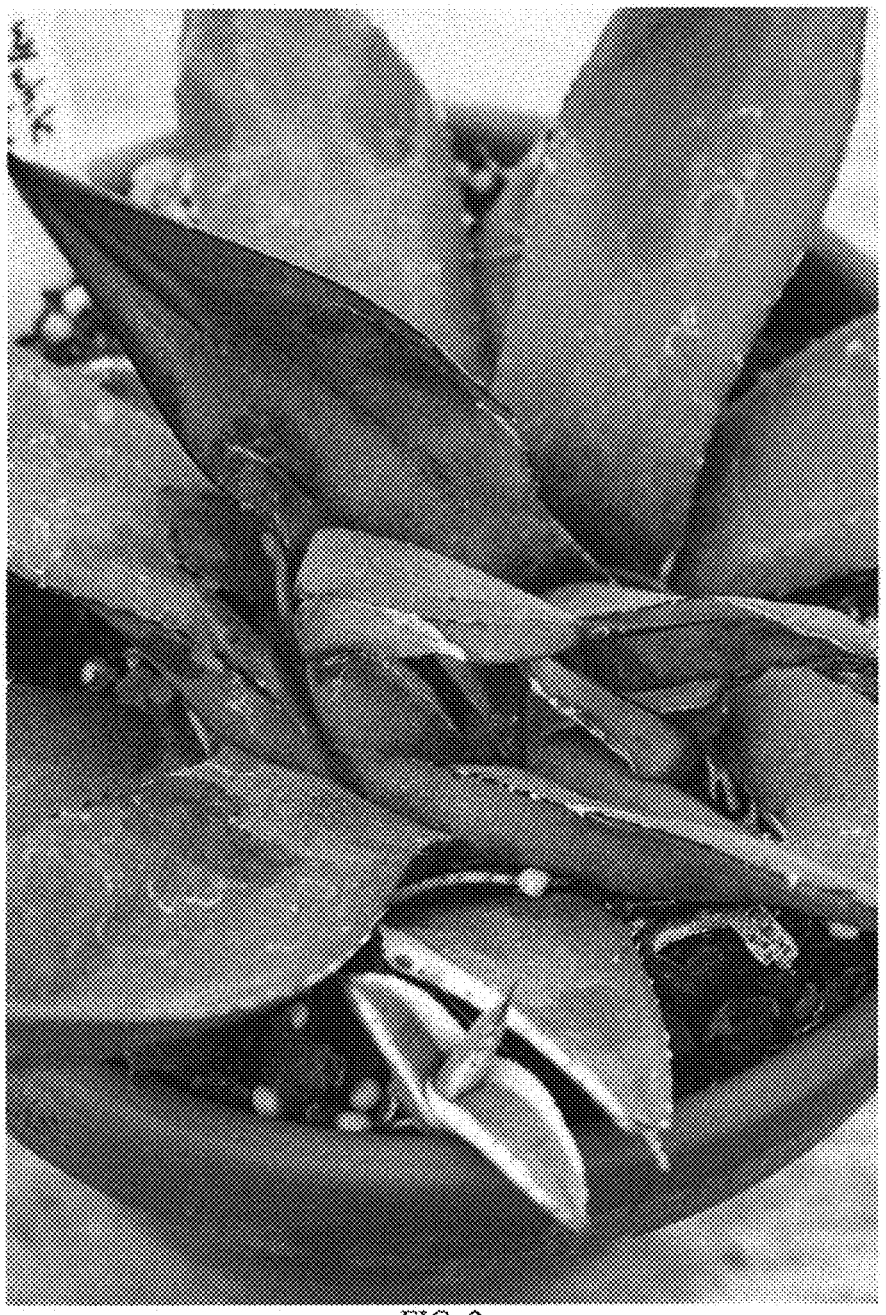
FIG. 2 shows the original sport as a mutation growing on the side of a plant of 'Sharkskin Shoes'.
Figure 3:
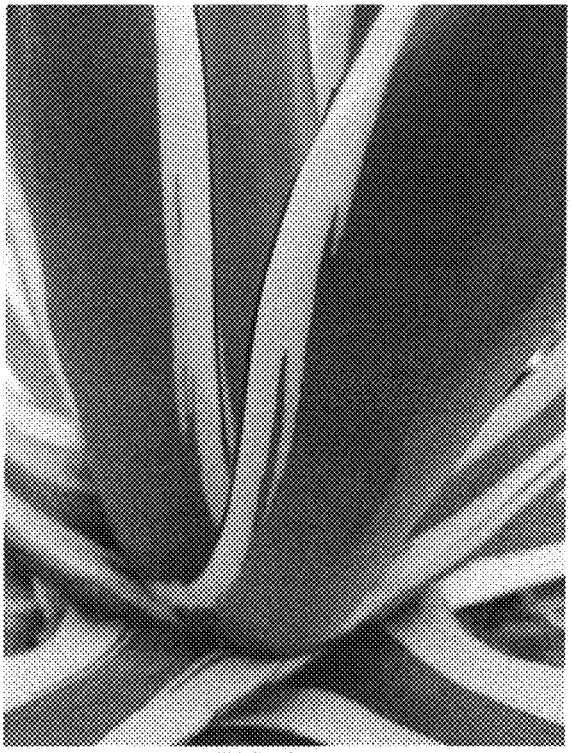
FIG. 3 shows a close-up of the back of the foliage of the new plant.
Figure 4:
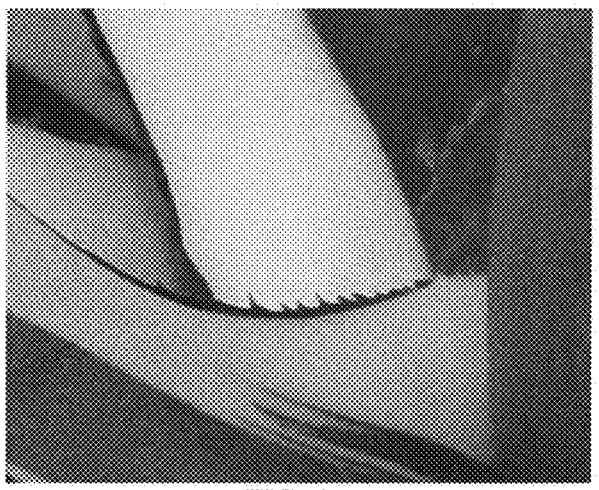
FIG. 4 shows the foliage with variegation and small marginal teeth near the base.

The following descriptions and color references are based on the 1995 edition of The Royal Horticultural Society Colour Chart, except where common dictionary terms are used. The new plant, *Agave* 'Great White Shark', has not been observed under all possible environments. The phenotype may vary slightly with different environmental conditions, such as temperature, light, fertility, moisture and maturity levels, but without any change in the genotype. The following observations and size descriptions are of a ten-year-old plant in a greenhouse in Raleigh, N.C. with supplemental water and fertilizer as needed.

Propagation: Division of basal offshoots;

Growth rate: Moderate to fast;

Crop time: About 24 to 32 weeks to finish during the summer in a 3.8 liter container from an established 2.5 cm tissue culture plug;

Rooting habit: Fleshy, lightly branching, with roots up to 40 cm long;

Root color: Nearest RHS Yellow-White Group 158A;

Plant shape and habit: Frost-tender herbaceous perennial with basal rosettes of narrow acaulescent leaves emerging from central base, producing a symmetrical rounded mound;

Plant size: Foliage height about 38.0 cm tall from soil line to the top of the leaves and about 69.0 cm to 76.0 cm wide at the widest point about 10 to 15 cm above soil line;

Foliage description: Linear to obovate; simple; fleshy; narrowly acute apex ending in long firm spine; truncate sessile base; margins toothed at base, entire to tip; glabrous and slightly glaucous adaxial and abaxial; upright to arching;

Number of leaves: About 20 to 25 per plant;

Leaf size: To about 30.0 cm to 32.0 cm long, 6.0 cm to 8.0 cm wide near center; dark gray-green center portion to 25.0 mm to 38.0 mm wide at longitudinal center of adaxial side, marginal variegation to 19.0 mm to 25.0 mm wide at longitudinal center of adaxial side and 22.0 mm thick near base;

Leaf variegation dimensions: Dark gray-green center portion to 25.0 mm to 38.0 mm wide at longitudinal center of adaxial side, marginal variegation to 19.0 mm to 25.0 mm wide at longitudinal center of adaxial side; abaxial dark gray-green center portion to 26.0 mm to 40.0 mm wide in longitudinal middle and abaxial marginal variegation to 16.0 mm to 22.0 mm wide in longitudinal middle; with occasional longitudinal stripes of bluish-green extending various random lengths into the intermediate zone;

Foliage fragrance: None observed;

Spine: Apical spine to about 19.0 mm to 38.0 mm long; firm and sharp; color on young leaves nearest RHS Greyed-Purple 187A, on mature leaves nearest RHS Greyed-Purple 187A;

Marginal teeth: Sharply pointed; firm; only in basal 8.0 cm; about 5.0 mm long and about 12.0 mm apart; color nearest RHS Greyed-Purple 187A;

Petiole: Sessile;

Stem: To about 12.0 cm to 15.5 cm wide and about 10.0 cm tall; covered with leaves;

Leaf blade color:

*Mature topside*.—Center nearest RHS Green-Group RHS 136B, margin nearest RHS Yellow Group 12C, region between margin and center (if different) nearest RHS 11A.

*Mature underside*.—Center nearest RHS Green Group 136B, margin nearest RHS Yellow Group 12C, region between margin and center (if different) nearest RHS 11A.

*Mature topside base*.—Center nearest RHS Green Group 136B, margin nearest RHS Yellow Group 12C.

*Mature underside base*.—Center nearest RHS Green Group 136B, center nearest RHS Yellow Group 12C.

*Expanding young topside*.—Center nearest RHS Green Group 136B, margin nearest RHS Yellow Group 12 and region between margin and center (if different) nearest RHS 144B.

*Expanding young underside*.—Center nearest RHS Green Group 136B, margin nearest RHS 12C and region between margin and center (if different) nearest RHS 144A; With a thin leaf edge of about 1 mm visible on both top and bottom nearest RHS 187A.

Veins: Indistinguishable;

Flower description: Flowers have not yet been observed;

Fruit and seed: Have not yet been observed;

Disease resistance: *Agave* 'Great White Shark' has not been observed to be resistant to diseases common to *Agaves* beyond that which is normal for *Agave*. The plant is xeromorphic and survives well with minimal water once established. Hardiness at least from USDA zone 9a to 10b. Full extent of winter hardiness has not been tested.

I claim:

1. A new and distinct cultivar of ornamental *Agave* plant named 'Great White Shark' as herein described and illustrated.

* * * * *